US010105439B2

(12) United States Patent
Hong et al.

(10) Patent No.: US 10,105,439 B2
(45) Date of Patent: *Oct. 23, 2018

(54) POLYSACCHARIDE FRACTION ORIGINATING IN PERSIMMON LEAF WITH IMMUNOSTIMULATING ACTIVATION AND ANTITUMOR ACTIVATION AND METHOD FOR MANUFACTURING SAME

(71) Applicants: KOREA FOOD RESEARCH INSTITUTE, Seongnam-si (KR); Kyonggi University Industry & Academy Cooperation Foundation, Suwon-si (KR)

(72) Inventors: Hee-Do Hong, Seongnam-si (KR); Young-Chul Lee, Seongnam-si (KR); Chang-Won Cho, Seoul (KR); Young-Kyoung Rhee, Seongnam-si (KR); Young-Chan Kim, Yongin-si (KR); Su Kyung Sung, Incheon (KR); Hee Jung Kim, Seoul (KR); Kwang-Soon Shin, Seoul (KR); Hye-Ryung Park, Suwon-si (KR); Sun Young Jo, Suwon-si (KR)

(73) Assignees: KOREA FOOD RESEARCH INSTITUTE, Seongnam-si (KR); Kyonggi University Industry & Academy Cooperation Foundation, Suwon-si (KR)

(*) Notice: Subject to any disclaimer, the term of this patent is extended or adjusted under 35 U.S.C. 154(b) by 206 days.

This patent is subject to a terminal disclaimer.

(21) Appl. No.: 14/871,220

(22) Filed: Sep. 30, 2015

(65) Prior Publication Data
US 2016/0015807 A1 Jan. 21, 2016

Related U.S. Application Data

(63) Continuation of application No. PCT/KR2013/012430, filed on Dec. 31, 2013.

(30) Foreign Application Priority Data

Apr. 2, 2013 (KR) ........................ 10-2013-0036024

(51) Int. Cl.
*A61K 39/39* (2006.01)
*A23L 33/10* (2016.01)
*A23L 33/105* (2016.01)
*A23L 33/22* (2016.01)
*A61K 39/00* (2006.01)

(52) U.S. Cl.
CPC .............. *A61K 39/39* (2013.01); *A23L 33/10* (2016.08); *A23L 33/105* (2016.08); *A23L 33/22* (2016.08); *A23V 2002/00* (2013.01); *A61K 2039/55583* (2013.01)

(58) Field of Classification Search
None
See application file for complete search history.

(56) References Cited

U.S. PATENT DOCUMENTS

| 5,240,732 A | 8/1993 | Ueda |
| 6,863,907 B2 | 3/2005 | Kotani et al. |
| 9,044,044 B2 | 6/2015 | Shin et al. |
| 2002/0009503 A1 | 1/2002 | Kotani et al. |
| 2007/0286938 A1 | 12/2007 | Saiki et al. |
| 2012/0270833 A1 | 10/2012 | Shin et al. |
| 2013/0150464 A1 | 6/2013 | Hishikawa et al. |

FOREIGN PATENT DOCUMENTS

| KR | 10-0726006 | 6/2007 |
| KR | 10-11168381 | 7/2012 |
| KR | 10-1201148 | 11/2012 |

OTHER PUBLICATIONS

Duan et al. International Journal of Biological Macromolecules 46; pp. 465-470. (Year: 2010).*
Akira et al., "Interleukin-6 in Biology and Medicine", Advances in Immunology, 1993, p. 1-78, vol. 54.
Dredge et al., "Adjuvants and the promotion of Th1-type cytokines in tumour immunotherapy", Cancer Immunology, Immunotherapy, Sep. 20, 2002, p. 521-531, vol. 51.
Romagne et al., "Natural killer cell-based therapies", F1000 Med Rep, May 3, 2011, p. 1-9, vol. 3, No. 9.
Ha et al., "Anti-Metastatic Activity of Glycoprotein Fractionated from Acanthopanax, Involvement of NK-cell and Macrophage Activation". Archives of Pharmacal Research, 2004, p. 217-224, vol. 27, No. 2.
Hirano et al, "Complementary DNA for a novel human interleukin (BSF-2) that induces B lymphocytes to produce immunoglobulin", Nature, Nov. 6, 1986, p. 73-76, vol. 324.
Hwang et al, "Characterization of Immuno-stimulating Polysaccharides Isolated from Korean Persimmon Vinegar", Korean Journal of Food Science and Technology, 2008, p. 220-227, vol. 40, No. 2.
Jung et al., "Purified Polysaccharide Activating the Complement System from Leaves of *Diospyos kaki* L.", Korean Journal of Food Science and Technology, 2002, p. 879-884, vol. 34, No. 5.
Kim et al., "TNFR-Fc fusion protein expressed by in vivo electroporation improves survival rates and myocardial injury in coxsackievirus induced murine myocarditis", Biochemical and biophysical research communications, Apr. 5, 2006, p. 765-771, vol. 344.
Kim, Seon-Gon, "Utilization and Mass Production on the Spodoptera litura Nucleopolyhedrovirus", Aug. 2002, p. 1-66.
Lotz et al., "B cell stimulating factor 2/interleukin 6 is a costimulant for human thymocytes and T lymphocytes.", The Journal of experimental medicine, Mar. 1, 1988, p. 1253-1258, vol. 167.

(Continued)

*Primary Examiner* — Amy L Clark
(74) *Attorney, Agent, or Firm* — H.C. Park & Associates, PLC

(57) ABSTRACT

A persimmon leaf-derived polysaccharide fraction consisting of 60-80 wt % of neutral sugar and 18-39 wt % of uronic acid, and 0.5-10 wt % of 3-deoxy-D-manno-2-octulosonic acid (KDO) analogs, the wt % based on the total weight of the polysaccharide fraction.

9 Claims, 8 Drawing Sheets

(56) References Cited

OTHER PUBLICATIONS

Mueller et al., "Chemical specificity of effector cell/tumor cell bridging by a Viscum album rhamnogalacturonan enhancing cytotoxicity of human NK cells", Immunopharmacology, 1990, p. 69-77, vol. 19.
Roder et al., "The biology of the human natural killer cell", Journal of clinical immunology, 1982, p. 249-263, vol. 2, No. 4.
Saiki et al., "Induction of tumoricidal macrophages and production of cytokines by synthetic muramyl dipeptide analogues", Vaccine, p. 238-244, Jun. 1988, vol. 6.
Yoon et al., "Anti-metastatic activity of Acanthopanax senticosus extract and its possible immunological mechanism of action", Journal of ethnopharmacology, p. 247-253, 2004, vol. 93.
International Search Report dated Mar. 31, 2014, in International Patent Application No. PCT/KR2013/012430.
Written Opinion of the International Search Authority dated Mar. 31, 2014, In International Patent Application No. PCT/KR2013/012430.
Kwon MH et al., Food Sci. Ind.; 30:30-43, 1997.
Non Final Office Action dated Feb. 13, 2017, in U.S. Appl. No. 14/307,933.
You Seon Sa, et al, "The Anticoagulant Fraction from the Leaves of *Diospyros kaki* L. Has an Antithrombotic Activity", Archives of Pharmacal Research http://apr.psk.or.kr, 2005, pp. 667-674, Arch Pharm Res, vol. 28, No. 6.
Third Office Action dated Dec. 21, 2017, issued in Chinese Patent Application No. 201380077143.6.
Shin et al., "Immuno-stimulating Activities of Polysaccharide Fractions 1 Isolated from Persimmon Leaves", The Korean Journal of Food and Nutrition, p. 941-950, vol. 25. No. 4, 2012.

\* cited by examiner

POLYSACCHARIDE FRACTION ORIGINATING IN PERSIMMON LEAF WITH IMMUNOSTIMULATING ACTIVATION AND ANTITUMOR ACTIVATION AND METHOD FOR MANUFACTURING SAME

CROSS-REFERENCE TO RELATED APPLICATIONS

This application is a continuation of International Application PCT/KR2013/012430, filed on Dec. 31, 2013, and claims priority from and the benefit of Korean Patent Application No. 10-2013-0036024, filed on Apr. 2, 2013, which are hereby incorporated by reference for all purpose as if fully set forth herein.

BACKGROUND

Field

The present disclosure relates to a persimmon leaf-derived polysaccharide fraction possessing immuno-stimulating and antitumor effects and a preparation method thereof.

Discussion of the Background

Persimmon leaves contain vitamin C of which content is 20 times higher than a lemon, and thus are used as health herbal tea. Persimmon leaves have the benefits of facilitating blood circulation, strengthening blood vessels, and being effective against scurvy, anemia, heart diseases, arteriosclerosis and cerebral hemorrhage. However, there have been little or no studies on the effects of persimmon leaves on the immune system.

Human beings have their own healing power which facilitates the overcoming of diseases naturally without external intervention. The tendency of increasing occurrence of various diseases in modern society is due to decrease in human healing power. However, human healing power has been weakening gradually since humans in modern society tend to depend on medications even for trivial conditions.

Immunity means the differentiation between self and non-self and the self-defense capability of a subject against both internal and external enemies. Health can be maintained through the immune system by which external enemies such as bacteria and viruses and internal enemies such as dead cells and abnormal cells among new cells derived from gene replication can be eliminated. Hence, it is natural that decreased immune function leads to an increased susceptibility to diseases. Further, immune function generally weakens along with aging.

In order to overcome any dysfunction of immune system, a variety of immune function stimulators have been developed and utilized. However, upon being used in long term, those substances tend to cause adverse side effects depending on different immunity in each individual. Particularly, while prevention is more important than treatment in immune-related diseases, currently available therapeutics are not suitable for the prevention of immune-related diseases. Therefore, there exists a strong need for natural therapeutics without adverse side effects.

Natural materials known to be involved in the activation of the immune system include lentinan isolated from *Lentinus edode*, polysaccharide K (PSK) isolated from *Coliolus versicolor* and so on.

Macrophages are the cells which secrete various cytokines and regulate immune conditions during the process of engulfing and digesting microorganisms and foreign substances, along with their pivotal role as an immune function against antigens. Macrophages are involved with antigen presentation and non-specific immune function of lymphocytes, in combination with their direct cytotoxicity on tumor cells. Furthermore, it has been reported that materials responding to TLR (Toll-like receptor) such as LPS or natural substances may activate macrophages, leading to the proliferation of T and B cells, the stimulation of macrophages for phagocytosis, and the production of cytokines such as IL-1, IL-6, IL-10, IL-12 and TNF-α known to regulate the secondary immune function against the infection of microorganisms.

Natural killer (NK) cells function to directly attack and kill cancerous cells or virus-infected cells through various mechanisms. These NK cells make up a small portion (5-10%) of total lymphocytes, but are the first responder with a potent capability to sense and remove abnormalities such as mutations in normal cells. In addition, NK cells, which are innate immune cells, play a very important role in regulating the functions of other immune cells and stimulating acquired immune cells to perform more potent defense action.

SUMMARY

Exemplary embodiments relate to a persimmon leaf-derived polysaccharide fraction possessing immuno-stimulating and antitumor effects and a preparation method thereof.

Additional aspects will be set forth in the detailed description which follows, and, in part, will be apparent from the disclosure, or may be learned by practice of the inventive concept.

An exemplary embodiment discloses a persimmon leaf-derived polysaccharide fraction consisting of 60-80 wt % of neutral sugar and 18-39 wt % of uronic acid, and 0.5-10 wt % of KDO (3-deoxy-D-manno-2-octulosonic acid) analogs. The wt % is based on the total weight of the polysaccharide fraction.

An exemplary embodiment also discloses a food composition for enhancing immunity including the persimmon leaf-derived polysaccharide fraction as an active ingredient.

An exemplary embodiment also discloses a pharmaceutical composition for enhancing immunity including the persimmon leaf-derived polysaccharide fraction as an active ingredient.

An exemplary embodiment also discloses a food composition for preventing or improving cancer including the persimmon leaf-derived polysaccharide fraction as an active ingredient.

An exemplary embodiment also discloses a pharmaceutical composition for preventing or treating a decreased immunity-caused disease selected from the group consisting of cold and chronic fatigue, the pharmaceutical composition including the persimmon leaf-derived polysaccharide fraction as an active ingredient.

An exemplary embodiment also discloses a pharmaceutical composition for preventing or improving cancer including the persimmon leaf-derived polysaccharide fraction as an active ingredient.

An exemplary embodiment also discloses an anti-cancer adjuvant preparation including the persimmon leaf-derived polysaccharide fraction as an active ingredient.

An exemplary embodiment also discloses a method for preparing a persimmon leaf-derived polysaccharide fraction, the method including: (a) treating a persimmon leaf powder with pectinase; and (b) collecting a fraction having a molecular weight of 3-300 kDa from an enzyme-treated persimmon leaf powder.

An exemplary embodiment also discloses a method for preparing a persimmon leaf-derived polysaccharide fraction, the method including: (a) treating a persimmon leaf powder with pectinase; and (b) collecting a fraction having a molecular weight of 3-300 kDa from an enzyme-treated persimmon leaf powder; and (c) collecting a fraction having a molecular weight of 5-30 kDa from the collected fraction in step (b).

An exemplary embodiment also discloses a method for enhancing immunity, the method including administering an effective amount of the persimmon leaf-derived polysaccharide fraction of claim 1 to a subject in need thereof.

An exemplary embodiment also discloses a method for preventing, improving and/or treating cancer, the method including administering an effective amount of the persimmon leaf-derived polysaccharide fraction of claim 1 to a subject in need thereof.

An exemplary embodiment also discloses a method for preventing and/or treating a decreased immunity-caused disease selected from the group consisting of cold and chronic fatigue, the method including administering an effective amount of the persimmon leaf-derived polysaccharide fraction of claim 1 to a subject in need thereof.

The foregoing general description and the following detailed description are exemplary and explanatory and are intended to provide further explanation of the claimed subject matter.

BRIEF DESCRIPTION OF THE DRAWINGS

FIG. 7A shows an inhibition rate of cancer metastasis upon the intravenous administration of PLW-0 and PLE-0 fractions, while

DETAILED DESCRIPTION OF THE ILLUSTRATED EMBODIMENTS

Figure 1:
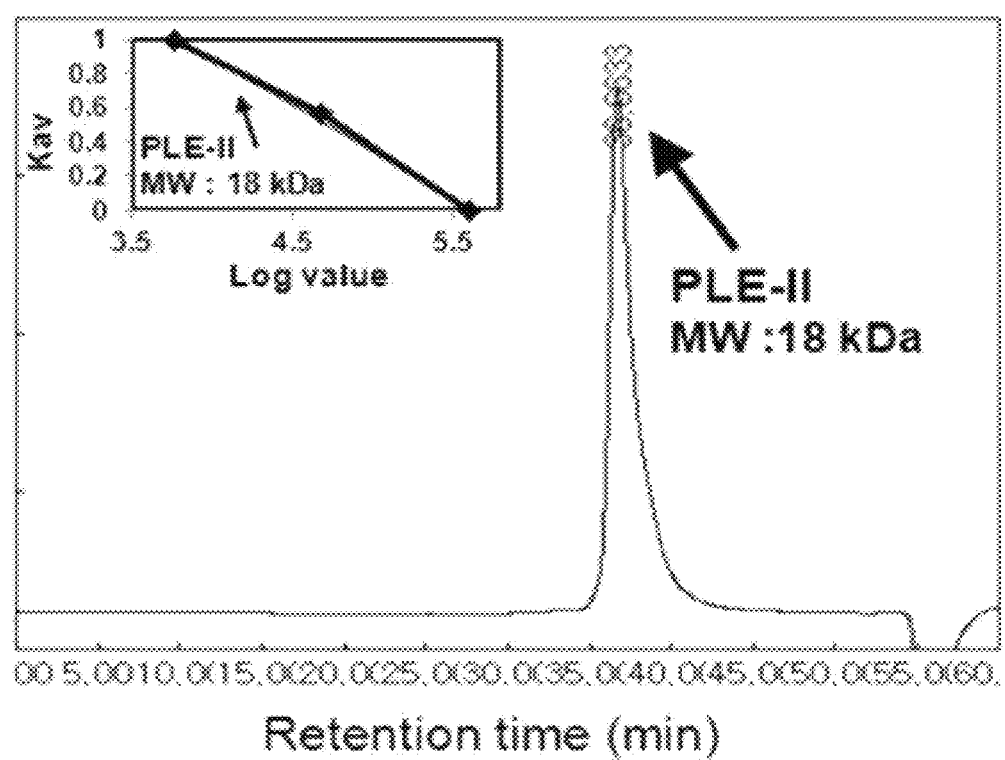
FIG. 1 is a result of HPLC spectrum for PLE-II fraction.

The inventors of the present disclosure have completed the present invention by finding out that a persimmon leaf-derived polysaccharide fraction stimulates the production of cytokines, and enhances the activity of Natural Killer (NK) cells and inhibits the metastasis of tumor cells.

An object of the present disclosure is to provide a persimmon leaf-derived polysaccharide fraction consisting of 60-80 wt % (based on the total weight of the polysaccharide fraction) of neutral sugar and 18-39 wt % of uronic acid, and 0.5-10 wt % of KDO (3-deoxy-D-manno-2-octulosonic acid) analogs.

Another object of the present disclosure is to provide a functional health food composition for enhancing immunity comprising the persimmon leaf-derived polysaccharide fraction as an active ingredient.

Still another object of the present disclosure is to provide a pharmaceutical composition for enhancing immunity comprising the persimmon leaf-derived polysaccharide fraction as an active ingredient.

Further object of the present disclosure is to provide a food composition for preventing or improving cancer comprising the persimmon leaf-derived polysaccharide fraction as an active ingredient.

Still further object of the present disclosure is to provide a pharmaceutical composition for preventing or treating a decreased immunity-caused disease selected from the group consisting of cold and chronic fatigue, comprising the persimmon leaf-derived polysaccharide fraction as an active ingredient.

Still another object of the present disclosure is to provide a pharmaceutical composition for preventing or treating cancer comprising the persimmon leaf-derived polysaccharide fraction as an active ingredient.

Still further object of the present disclosure is to provide an anti-cancer adjuvant preparation comprising the persimmon leaf-derived polysaccharide fraction as an active ingredient.

Still further object of the present disclosure is to provide a method for preparing a persimmon leaf-derived polysaccharide fraction, comprising
(a) treating a persimmon leaf powder with pectinase; and
(b) collecting a fraction having a molecular weight of 3-300 kDa from the enzyme-treated persimmon leaf powder.

Still further object of the present disclosure is to provide a method for preparing a persimmon leaf-derived polysaccharide fraction, comprising
(a) treating a persimmon leaf with pectinase;
(b) collecting a fraction having a molecular weight of 3-300 kDa from the enzyme-treated persimmon leaf and
(c) collecting a fraction having a molecular weight of 5-30 kDa from the collected fraction in step (b).

Still another object of the present disclosure is to provide a use of the persimmon leaf-derived polysaccharide fraction for the preparation of an agent for enhancing immunity.

Still another object of the present disclosure is to provide a use of the persimmon leaf-derived polysaccharide fraction for the preparation of an agent for treating a decreased immunity-caused disease selected from the group consisting of cold and chronic fatigue.

Still another object of the present disclosure is to provide a use of the persimmon leaf-derived polysaccharide fraction for the preparation of an anti-cancer agent.

Further another object of the present disclosure is to provide a method for enhancing immunity comprising administering an effective amount of the persimmon leaf-derived polysaccharide fraction to a subject in need thereof.

Still further another object of the present disclosure is to provide a method for preventing, improving and/or treating cancer comprising administering an effective amount of the persimmon leaf-derived polysaccharide fraction to a subject in need thereof.

Still further another object of the present disclosure is to provide a method for preventing and/or treating a decreased immunity-caused disease selected from the group consisting of cold and chronic fatigue, comprising administering an effective amount of said persimmon leaf-derived polysaccharide fraction to a subject in need thereof.

To achieve the above mentioned object, the present disclosure describes a persimmon leaf-derived polysaccharide fraction consisting of 60-80 wt % (based on the total weight of the polysaccharide fraction) of neutral sugar and 18-39 wt % of uronic acid, and 0.5-10 wt % of KDO (3-deoxy-D-manno-2-octulosonic acid) analogs.

To achieve the above another object, the present disclosure describes a food composition for enhancing immunity comprising the persimmon leaf-derived polysaccharide fraction as an active ingredient.

To achieve the above another object, the present disclosure describes a food composition for preventing or improving cancer comprising the persimmon leaf-derived polysaccharide fraction as an active ingredient.

To achieve the above another object, the present disclosure describes a pharmaceutical composition for preventing or treating a decreased immunity-caused disease selected from the group consisting of cold and chronic fatigue, comprising the persimmon leaf-derived polysaccharide fraction as an active ingredient.

To achieve the above another object, the present disclosure describes a pharmaceutical composition for preventing or treating cancer comprising the persimmon leaf-derived polysaccharide fraction as an active ingredient.

To achieve the above another object, the present disclosure describes an anti-cancer adjuvant preparation comprising the persimmon leaf-derived polysaccharide fraction as an active ingredient.

To achieve the above another object, the present disclosure describes a method for preparing a persimmon leaf-derived polysaccharide fraction, comprising
(a) treating a persimmon leaf with pectinase; and
(b) collecting a fraction having a molecular weight of 3-300 kDa from the enzyme-treated persimmon leaf.

To achieve the above another object, the present disclosure describes a method for preparing a persimmon leaf-derived polysaccharide fraction, comprising
(a) treating a persimmon leaf with pectinase;
(b) collecting a fraction having a molecular weight of 3-300 kDa from the enzyme-treated persimmon leaf and
(c) collecting a fraction having a molecular weight of 5-30 kDa from the collected fraction in step (b).

To achieve the above another object, the present disclosure describes a use of the persimmon leaf-derived polysaccharide fraction for the preparation of an agent for enhancing immunity.

To achieve the above another object, the present disclosure describes a use of the persimmon leaf-derived polysaccharide fraction for the preparation of an agent for treating a decreased immunity-caused disease selected from the group consisting of cold and chronic fatigue.

To achieve the above another object, the present disclosure describes a use of the persimmon leaf-derived polysaccharide fraction for the preparation of an anti-cancer agent.

To achieve the above another object, the present disclosure describes a method for enhancing immunity comprising administering an effective amount of the persimmon leaf-derived polysaccharide fraction to a subject in need thereof.

To achieve the above another object, the present disclosure describes a method for preventing, improving and/or treating cancer comprising administering an effective amount of the persimmon leaf-derived polysaccharide fraction to a subject in need thereof.

To achieve the above another object, the present disclosure describes a method for preventing and/or treating a decreased immunity-caused disease selected from the group consisting of cold and chronic fatigue, comprising administering an effective amount of the persimmon leaf-derived polysaccharide fraction to a subject in need thereof.

Exemplary embodiments will be described in detail as follows.

The present disclosure provides a persimmon leaf-derived polysaccharide fraction consisting of 60-80 wt % (based on the total weight of the polysaccharide fraction) of neutral sugar and 18-39 wt % of uronic acid, and 0.5-10 wt % of KDO (3-deoxy-D-manno-2-octulosonic acid) analogs.

The total polysaccharide fraction according to an exemplary embodiment consists of neutral sugar, uronic acid, KDO analogs and proteins.

The "uronic acid" as used herein is characterized by consisting of galacturonic acid and glucuronic acid. The "KDO analogs" as used herein is characterized by consisting of DHA (3-deoxy-D-lyxo-2-heptulosaric acid) and KDO (3-deoxy-D-manno-2-octulosonic acid). However, aspects are not necessarily limited as such.

Moreover, the "neutral sugar" as used herein is characterized by comprising arabinose, rhamnose, galactose, fucose, glucose, and Rhamnogalacturonan-II indicator polysaccharides. However, aspects are not necessarily limited as such.

Preferably, the "neutral sugar" as used herein is characterized by consisting of, based on the total mole of the neutral sugar in the a persimmon leaf-derived polysaccharide fraction, 20-40 mole % of arabinose, 10-40 mole % of rhamnose, 10-40 mole % of galactose, 1-10 mole % of fucose, 1-10 mole % of glucose, and 0.4-26 mole % of Rhamnogalacturonan-II indicator polysaccharides. However, aspects are not necessarily limited as such.

The "Rhamnogalacturonan-II indicator polysaccharides" as used herein are characterized by consisting of, based on the total mole of the neutral sugar in the a persimmon leaf-derived polysaccharide fraction, 0.1-8 mole % of methylfucose, 0.1-8 mole % of methylxylose, 0.1-5 mole % of apiose, and 0.1-5 mole % of aceric acid. However, aspects are not necessarily limited as such.

The persimmon leaf-derived polysaccharide fraction according to an exemplary embodiment is obtained by a method comprising (a) treating a persimmon leaf powder with pectinase; and (b) collecting a fraction having a molecular weight of 3-300 kDa from the enzymatic hydrolysate of the persimmon leaf.

Particularly, the persimmon leaf-derived polysaccharide fraction according to an exemplary embodiment is obtained by treating a persimmon leaf with pectinase in step (a). The persimmon leaf may be dried or undried persimmon leaf, while being pulverized or powdered form.

In step (b), a fraction having a molecular weight of 3-300 kDa is collected from the enzymatically treated persimmon leaf.

The persimmon leaf-derived fractions obtained by the treatment of pectinase were followed by ultra-filtration to remove the fractions having a molecular weight of under 3 kDa and above 300 kDa, resulting in persimmon leaf-derived crude polysaccharide fraction (PLE-0). Components of the obtained fraction (PLE-0) were analyzed by gas chromatography, finding that the fraction consisted of 71.3 wt % (based on the total weight of the polysaccharide fraction) of neutral sugar, 26.2 wt % of uronic acid, 0.7 wt % of protein, and 1.8 wt % of KDO analogs. Upon analyzing the components of the neutral sugar in said fraction, based on the total mole of the neutral sugar, 1.6 mole % of 2-methylfucose, 15.6 mole % of rhamnose, 2.4 mole % of fucose, 2.0 mole % of 2-methylxylose, 26.3 mole % of arabinose, 6.7 mole % of xylose, 4.5 mole % of apiose, 1.4 mole % of aceric acid, 2.1 mole % of mannose, 32.3 mole % of galactose, and 5.1 mole % of glucose were detected. Among said neutral sugar components, 2-methylfucose, 2-methylxylose, apiose, and aceric acid are included as Rhamnogalacturonan-II (RG-II) indicator materials (See Example 2-1 and Table 2). The KDO analogs, i.e. KDO (3-deoxy-D-manno-2-octulosonic acid) and DHA (3-deoxy-D-lyxo-2-heptulosaric acid) are also RG-II indicator materials.

In step (c), a fraction having a molecular weight of 5-30 kDa is further collected from the collected fraction in step (b).

That is, ultra-filtration was performed on the fraction obtained in step (b), collecting a fraction having a molecular weight of 5-30 kDa (PLE-II). Components of the obtained fraction (PLE-II) were analyzed by gas chromatography, finding that the fraction consisted of 69.5 wt % (based on the total weight of the polysaccharide fraction) of neutral sugar, 27.2 wt % of uronic acid, and 3.3 wt % of KDO analogs. Upon analyzing the components of the neutral sugar in said fraction, based on the total mole of the neutral sugar, 4.0 mole % of 2-methylfucose, 27.9 mole % of rhamnose, 4.9 mole % of fucose, 4.7 mole % of 2-methylxylose, 28.2 mole % of arabinose, 2.9 mole % of apiose, 3.5 mole % of aceric acid, 0.4 mole % of mannose, 19.6 mole % of galactose, and 3.9 mole % of glucose were detected. Among said neutral sugar components, 2-methylfucose, 2-methylxylose, apiose, and aceric acid are included as Rhamnogalacturonan-II (RG-II) indicator materials (See Example 2-1 and Table 2). The KDO analogs, i.e. KDO (3-deoxy-D-manno-2-octulosonic acid) and DHA (3-deoxy-D-lyxo-2-heptulosaric acid) are also RG-II indicator materials.

It has been reported that pectic substances are complex structured polysaccharides mainly found in primary cell walls and middle lamellas of higher plants. Most molecules of pectin are composed of homogalacturonan (See Kwon M H et al., Food Sci. Ind.; 30:30-43, 1997), while being covalently bonded with various oligo- and polysaccharide-branched rhamnogalacturonan-I (RG-I) and rhamnogalacturonan-II (RG-II) (See Kim J M et al., Biochem. Bioph. Res. Co.; 344:765-771, 2006).

The persimmon leaf-derived polysaccharide fraction according to an exemplary embodiment possesses an immune-stimulating activity.

Upon evaluating the activity of the persimmon leaf-derived polysaccharide fraction (PLE-II) according to an exemplary embodiment in enhancing the production of cytokines, it was found to stimulate the production of IL (interleukin)-6 and IL-12. Regarding IL-6, the fraction PLE-II in its concentration of 4.0 μg/ml to 100 μg/ml showed a high capability of producing IL-6 which was comparable to that of the positive control group, i.e. LPS (lipopolysaccharide). Even though the hot water extract (PLW) and the crude polysaccharide fraction obtained from the enzymatic treatment (PLE-0) also increased the production of IL-6 proportionally in dose-dependent manner, the production of IL-6 stimulated by them in their concentration of 100 μg/ml or less was much lower than that of the fraction PLE-II. Hence, it suggests that the persimmon leaf-derived polysaccharide fraction (PLE-II) according to an exemplary embodiment even in its small amount is significantly effective in the production of IL-6. Regarding IL-12, it was found that the fraction PLE-II was overall more effective in stimulating the expression level of IL-12 than PLW and PLE-0, even though it increased the production of IL-20 proportionally in dose-dependent manner until its concentration reached 20.0 μg/ml, followed by the decrease of its effect in its concentration of larger than 20.0 μg/ml. In case of TNF-α, it was found that its expression level changed similarly, while increasing proportionally in dose-dependent manner until the concentration of the fraction PLE-II reached 100 μg/ml (See Example 4 and FIG. 3).

IL-6, IL-12 and TNF-α, which are representative cytokines induced by macrophages, are known to play a crucial role in inflammatory responses caused by bacterial infection and increase in their expression levels at the sites of inflammation. IL-6 is a cytokine also called "B cell-stimulating factor 2 (BSF2)" or "interferon β2". IL-6 was discovered as a differentiation factor involved in the activation of B lymphocytes (See Hirano, T. et al., Nature 324, 73-76, 1986), followed by a clear finding that it influences the functions of various cells as a multifunctional cytokine (See Akira, S. et al, Adv. in Immunology, 54, 1-78, 1993).

Figure 2:
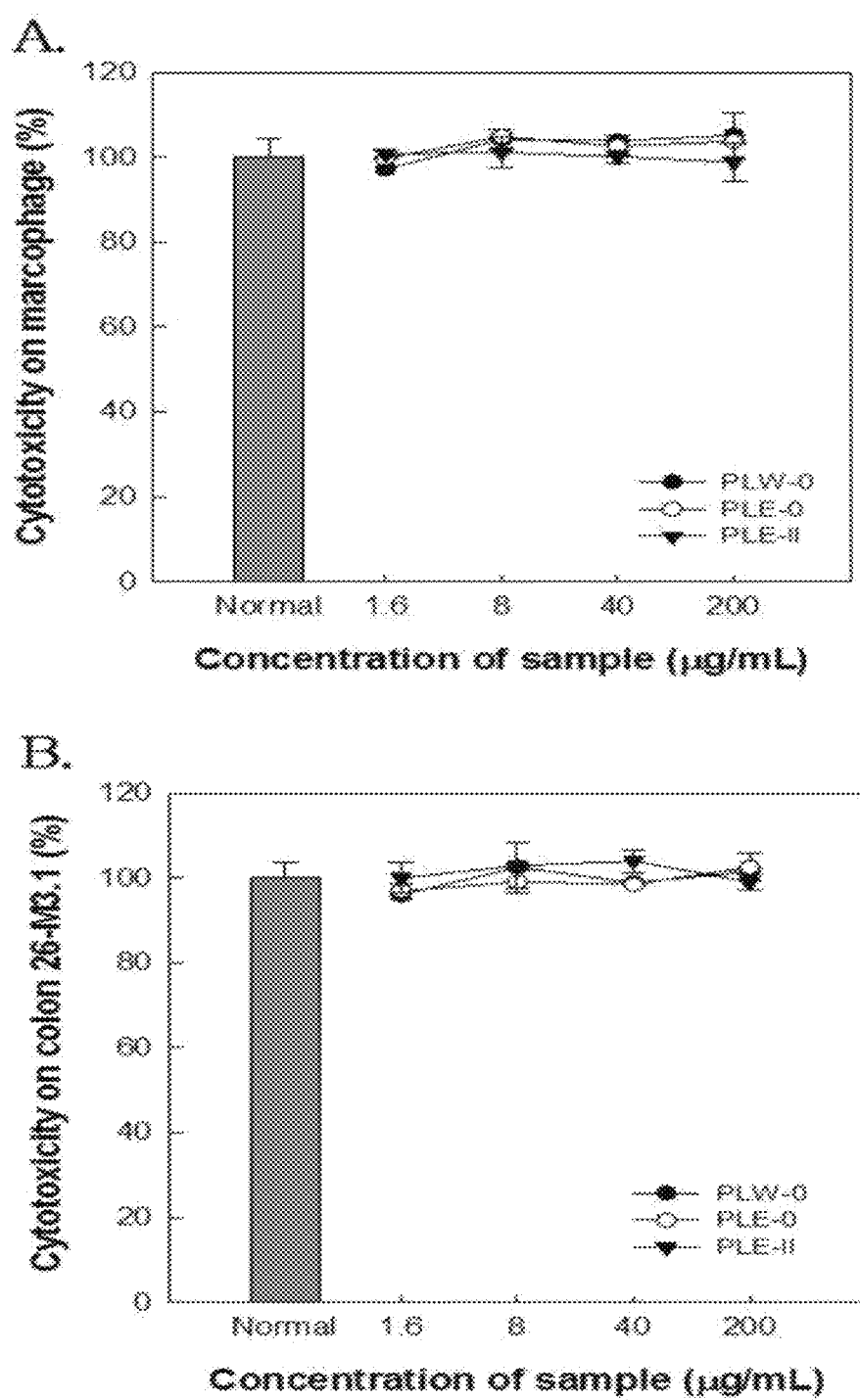
FIG. 2 shows (a) a test result regarding the cytotoxicity of PLE-II fraction on macrophages (Cytotoxicity on macrophage (%): the survival rate of macrophages; concentration of sample (μg/ml): the concentration of PLE-II with which was treated on macrophages; Normal: macrophage control group which was not treated with PLE-II), and (b) a test result regarding the cytotoxicity of PLE-II on tumor cells (Cytotoxicity on Colon 26-M3.1(%): the survival rate of tumor cells; concentration of sample (μg/ml): the concentration of PLE-II with which was treated on tumor cells; Normal: tumor cell control group which was not treated with PLE-II).

In addition, a cytotoxicity test on macrophages as performed showed that the persimmon leaf-derived polysaccharide fraction according to an exemplary embodiment did not cause a significant iii cytotoxicity even in its maximal concentration of 200 μg/ml (See Example 3 and FIG. 2). Furthermore, the persimmon leaf-derived polysaccharide fraction according to an exemplary embodiment affects the activation of NK cells (Natural Killer cells). In order to measure its influence on the activation of NK cells, the persimmon leaf-derived polysaccharide fraction according to an exemplary embodiment in a concentration of 2 mg/kg was intravenously injected into test mice. Subsequently, their spleens were extracted and NK cells were prepared, followed by being mixed with cancer cells based on E/T ratio. The cytotoxicity of NK cells against cancer cells was evaluated, finding that as E/T ratio became higher, their activity got stronger. The persimmon leaf-derived polysaccharide fraction according to an exemplary embodiment showed higher cytotoxicity on cancer cells by 26% or more, in comparison with the control group which was not treated with the persimmon leaf-derive polysaccharide fraction. The "E/T ratio" refers to a ratio in terms of the number or the concentration of Effector cell to that of Target cell. As described in Example 5 of the present disclosure, splenocytes were used as Effector cells, while cancer cells YAC-1 were used as Target cells (See FIG. 4).

Also, in order to check the effect of the persimmon leaf-derived polysaccharide fractions on the activation of NK cells upon their oral administration, test substances were orally administered in their concentrations of 10 and 100 μg/mouse, respectively, once daily for 20 days. After mice were sacrificed, their spleen-derived NK cells were tested to evaluate their cytotoxic effects on tumor cells Yac-1. The effects of PLW-0 and PLE-0 in the activation of NK cells showed their cytotoxic effects on tumor cells in an E/T ratio-dependent manner. Based on 50:1 of E/T ratio, PLW-0 showed its cytotoxicity rate of 19.1% and 21.0% in its concentration of 10 μg and 100 μg, respectively, whereas PLE-0 showed its cytotoxicity rate of 20.9% and 22.7%, respectively. This result confirmed that the cytotoxicity of PLE-0 fraction as prepared by the enzymatic treatment and the molecular weight fraction was higher than that of the simple hot water extracted polysaccharide fraction PLW-0. E/T ratios of 25:1 and 100:1 showed similar tendency, respectively. As a result, it was confirmed that the oral administration of the persimmon leaf-derived polysaccharide fraction also influenced the activation of NK cells which are cytotoxic to tumor cells (See FIG. 6).

Macrophages are the cells which secrete various cytokines and regulate immune conditions during the process of engulfing and digesting microorganisms and foreign substances, along with their crucial role as an immune function against antigens. Macrophages are involved with antigen presentation and non-specific immune function of lymphocytes, in combination with their direct cytotoxicity against tumor cells.

Natural killer (NK) cells function to directly attack and kill cancerous cells or virus-infected cells through various mechanisms. These NK cells make up a small portion (5-10%) of total lymphocytes, but have a potent function to sense and remove abnormalities such as mutations in normal cells. In addition, NK cells play a crucial role in regulating the functions of other immune cells, while, as an innate immune cell, also stimulating acquired immune cells to perform more potent defense action. In normal persons, genetic and environmental factors are primarily removed by NK cells.

The persimmon leaf-derived polysaccharide fraction according to an exemplary embodiment is characterized by its activity of inhibiting the metastasis of cancer.

In order to evaluate the anti-metastatic activity of the persimmon leaf-derived polysaccharide fraction when a tumor spreads to other organs of the body, its in-vivo activity was measured using a lung-metastasized model of Colon 26-M3.1 carcinoma cell line. Based on the result that an average of about 120 colonies were counted in the tumor control group, the metastasis rates of the persimmon leaf-derived simple water-extracted crude polysaccharide fraction (PLW-0), the enzymatic treated-crude polysaccharide fraction (PLE-I), and the enzymatic treated-crude purified polysaccharide fraction (PLE-II) were measured, respectively. The results revealed that the polysaccharide fraction (PLE-II) according to an exemplary embodiment showed the strongest activity in inhibiting the metastasis of cancer in its all levels of tested concentrations (See Example 6 and FIG. 5). Especially, considering that the polysaccharide fraction (PLE-II) according to an exemplary embodiment was found markedly effective than other fractions in its smallest dose of 10 μg, it is suggested that even its small amount is more potent than other fractions.

In addition, in order to compare the anti-metastatic activities of the persimmon leaf-derived fractions prior to and after the enzymatic treatment and the molecular weight-based fraction process, test materials were intravenously injected in a dosage amount of 10, 100 and 1,000 μg/mouse two (2) days prior to the administration of tumor, or orally administered in a dosage amount of 10 μg/mouse once a day for 20 days prior to the injection of tumor to six week old female BALB/c mice, respectively. Then, Colon 26-M3.1 carcinomas were injected intravenously to said mice, followed by extracting a target organ, i.e. the lung from each test mouse 14 days after the tumor administration and counting the tumor colonies in the lung. As a result, in the case of the intravenous injection of 10 μg, PLW-0 fraction showed 30.2% of anti-metastatic effect compared with the non-substance administered control group, while PLE-0 fraction showed 63.5% which was around two times higher than that of PLW-0 fraction. In the case of the intravenous injection of 1000 μg, PLW-0 fraction showed around 71.7% of anti-metastatic effect, while PLE-0 fraction showed around 87.7%. The above described results demonstrate that the enzymatically treated crude polysaccharide fraction possesses a noticeably increased anti-metastatic effect, in comparison with the polysaccharide fraction obtained through the simple hot water extraction. In the case of the oral administration of the persimmon leaf-derived polysaccharide fraction, the hot water-extracted polysaccharide fraction (PLW-0) showed 47.1% of anti-metastatic effect, while the enzymatically treated polysaccharide fraction (PLE-0) showed 70% of anti-metastatic effect (See Example 6-2 and FIG. 7A and FIG. 7B).

The persimmon leaf-derived polysaccharide fraction according to an exemplary embodiment stimulates cytokines including IL-6, IL-12 and TNF-α, is not significantly cytotoxic to macrophages, enhances the activity of Natural Killer cells to improve their effect in inducing the killing of tumor cells, and inhibits the metastasis of tumor cells. Hence, the persimmon leaf-derived polysaccharide fraction is effective in enhancing immunity and preventing or treating cancer.

Therefore, the present disclosure provides a food composition for enhancing immunity comprising the persimmon leaf-derived polysaccharide fraction as an active ingredient. Further, the present disclosure provides a food composition for preventing or improving cancer.

The term "enhancing immunity" as used herein means to increase the immune response or activity of immune system in the body.

The food composition according to an exemplary embodiment includes all types of preparations such as a functional food, a nutritional supplement, a health food, and a food additive. The said food composition may be prepared into various kinds of preparations by the methods known in the art.

For example, as a health food, a persimmon leaf-derived polysaccharide fraction according to an exemplary embodiment may be prepared into tea, juice or drink for beverages, or may be prepared into granules, capsules or powder for intake. Also, conventional active ingredients which are well known as having an activity in enhancing immunity or preventing or treating cancer may be mixed with the persimmon leaf-derived polysaccharide fraction so as to prepare in a form of composition.

Further, for preparing a functional food, a persimmon leaf-derived polysaccharide fraction according to an exemplary embodiment may be added to beverages (including alcoholic beverages), fruits, and their processed foods (e.g. canned fruit, bottled fruit, jam, marmalade etc.), fishes, meats, and their processed foods (e.g. ham, sausage, corn beef etc.), breads and noodles (e.g. Japanese noodle, buckwheat iii noodle, ramen, spaghetti, macaroni etc.), fruit juice, drinks, cookies, toffee, dairy products (e.g. butter, cheese etc.), vegetable oil, margarine, vegetable protein, retort food, frozen food, various seasonings (e.g. soybean paste, soybean sauce, sauce etc.).

The said food composition comprises preferably, but is not limited to, 0.01 to 100 weight % (based on the total weight of a food product) of the persimmon leaf-derived polysaccharide fraction.

As a food additive, the persimmon leaf-derived polysaccharide fraction may be prepared into a form of powder or concentrated liquid.

Also, the present disclosure provides an anti-cancer adjuvant preparation comprising said persimmon leaf-derived polysaccharide fraction as an active ingredient. As used herein, the anti-cancer adjuvant preparation means an adjuvant preparation which functions to enhance and restore an immune function during an anticancer treatment.

Further, the present disclosure provides a pharmaceutical composition for preventing or treating a disease caused by decreased immunity, which is selected from the group consisting of cold and chronic fatigue, the composition comprising said persimmon leaf-derived polysaccharide fraction as an active ingredient. The expression "disease caused by decreased immunity" means either a disease that is more easily caused by a decrease in an immune function compared to normal persons, or a disease difficult to treat due to a decrease in immune function.

The present disclosure provides a pharmaceutical composition for preventing or treating cancer. As used herein, the term "cancer", in its narrower sense, means a cancer caused by the decreased activity of NK cells. NK cells function to kill cancerous cells detected in their early stages, and directly attack cancerous cells to induce their death or apoptosis, resulting in preventing their relapse and metastasis. The persimmon leaf-derived polysaccharide fraction according to an exemplary embodiment functions to enhance the cancer cell cytotoxicity of NK cells. Also, the pharmaceutical composition for preventing or treating cancer may be a composition for inhibiting cancer metastasis in its narrower sense. The persimmon leaf-derived polysaccharide fraction according to an exemplary embodiment showed its activity of inhibiting cancer metastasis.

The term "cancer" as used herein is selected from the group consisting of colon cancer, lung cancer, liver cancer, gastric cancer, esophageal cancer, pancreatic cancer, gall bladder cancer, renal cancer, bladder cancer, prostatic cancer, testicular cancer, cervical cancer, endometrial cancer, choriocarcinoma, ovarian cancer, breast cancer, thyroid cancer, brain cancer, head and neck cancer, malignant melanoma, lymphoma, aplastic anemia, hematological cancer.

The present disclosure provides a use of said persimmon leaf-derived polysaccharide fraction for the preparation of an agent for enhancing immunity.

Further, the present disclosure provides a use of said persimmon leaf-derived polysaccharide fraction for the preparation of an agent for treating a decreased immunity-caused disease selected from the group consisting of cold and chronic fatigue.

Furthermore, the present disclosure provides a use of said persimmon leaf-derived polysaccharide fraction for the preparation of an anti-cancer agent.

The present disclosure provides a method for enhancing immunity comprising administering an effective amount of said persimmon leaf-derived polysaccharide fraction to a subject in need thereof.

Further, the present disclosure provides a method for preventing, improving and/or treating cancer comprising administering an effective amount of said persimmon leaf-derived polysaccharide fraction to a subject in need thereof.

Furthermore, the present disclosure provides a method for preventing and/or treating a decreased immunity-caused disease selected from the group consisting of cold and chronic fatigue, comprising administering an effective amount of said persimmon leaf-derived polysaccharide fraction to a subject in need thereof.

As used herein, the "effective amount" refers to the amount showing the effect on enhancing immunity, and preventing and treating cancer or a disease caused by decreased immunity, upon being administered to a subject. As used herein, the "subject" refers to animals, preferably mammalians, particularly mammalians including humans, while cells, tissues or organs of an animal origin are also included. The subject may be a patient in need of treatment.

In the pharmaceutical composition according to an exemplary embodiment for preventing and treating cancer or a disease caused by decreased immunity, the polysaccharide fraction or its pharmaceutically acceptable salt may be contained alone or in mixture with one or more pharmaceutically acceptable carrier, excipient or diluent.

As a pharmaceutically acceptable carrier, for example, carriers for parenteral or oral preparations may be further comprised. The carriers for the oral preparations may include lactose, starch, cellulose derivatives, magnesium stearate, and stearic acid. The carriers for the parenteral preparations may include water, suitable oil, saline, aqueous glucose and glycol. Stabilizers or preservatives may be further comprised. The examples of suitable stabilizers are an antioxidant such as sodium hydrogen sulfite, sodium sulfite, and ascorbic acid. The examples of suitable preservatives are benzalkonium chloride, methyl- or prophylparaben, and chlorobutanol. The list of pharmaceutically acceptable carriers is disclosed in Remington's Pharmaceutical Sciences, 19th ed., Mack Publishing Company, Easton, Pa., 1995.

The pharmaceutical composition may be administered to mammalians including human beings by various routes. For example, it may be administered via oral or parenteral route. A parenteral administration includes, but is not limited to, intravenous, intramuscular, intra-arterial, intramarrow, subdural, intracardiac, transdermal, subcutaneous, intraperitoneal, intranasal, intra-gastrointestinal tract, topical, sublingual or rectal administration. The pharmaceutical composition according to an exemplary embodiment may be preferably administered transdermally. As used herein, the term "transdermal administration" means that the pharmaceutical composition is administered into a cell or the skin, thereby rendering the active ingredient as contained in the composition delivered into the skin. For instance, the pharmaceutical composition may be prepared into an injectable formulation, and then administered by lightly pricking the skin with a 30 gauge thin injection needle or by a direct application onto the skin.

A pharmaceutical composition may be formulated in the form of oral preparation or parenteral preparation according to the above described administration routes.

In case of a formulation for oral administration, the composition may be formulated into powders, granules, tablets, pills, sugar-coated tablets, capsules, liquids, gels, syrups, slurries, and emulsions by the methods well known in the art. For example, preparations for oral administration may be obtained in the form of tablets or sugar-coated tablets by mixing an active ingredient with a solid excipient, grinding, and adding appropriate supplemental agents, then manufacturing a form of granular mixture. Examples of suitable excipients are sugars including lactose, dextrose, sucrose, sorbitol, mannitol, xylitol, erythritol and maltitol; starches including corn starch, wheat starch, rice starch and potato starch; celluloses including cellulose, methyl cellulose, sodium carboxymethylcellulose and hydroxypropylmethylcellulose; and fillers including gelatin and polyvinylpyrrolidone. Further, if desired, cross-linked polyvinylpyrrolidone, agar, alginic acid or sodium alginate may be added as a solutionizer. Still further, the pharmaceutical composition may additionally comprise anti-coagulating agents, lubricants, wetting agents, flavoring agents, emulsifying agents and antiseptics.

In case of a formulation for parenteral administration, it may be prepared into the form of injectable preparations, creams, lotions, ointments, oils, humectant, gels, aerosol, and nasal inhalants according to the methods well known in the art. The above-mentioned formulations are well described in Remington's Pharmaceutical Science, 15th Edition, 1975. Mack Publishing Company, Easton, Pa. 18042, Chapter 87: Blaug, Seymour which is well known prescription book.

Total effective amount of pharmaceutical composition according to an exemplary embodiment may be administered to a patient in a single dose, or may be administered in multiple doses by fractionated treatment protocol. The pharmaceutical composition may contain variable amount of an active ingredient according to the disease severity. The total dose of the polysaccharide fraction according to an exemplary embodiment may be preferably about 0.01 µg to 1000 mg/kg body weight/day, more preferably 0.1 µg to 100 mg/kg body weight/day, and most preferably 0.1 µg to 10 mg/kg body weight/day. However, the dose of the polysaccharide fraction according to an exemplary embodiment may be suitably determined by considering various factors, such as age, body weight, health condition, sex, disease severity, diet and excretion of a patient, as well as administration route and frequency. When those factors are considered, skilled persons in the art may determine appropriate dose of the polysaccharide fraction according to an exemplary embodiment for a certain use as an immunity-enhancing agent. The pharmaceutical composition may not be limited in terms of the types of formulation, administration routes, and administration methods as long as they exert the advantageous effect(s) described in the present disclosure.

NK cells, of which activity may be enhanced by the persimmon leaf-derived polysaccharide fraction according to an exemplary embodiment, has been reported as innate immune cells exerting a potent immune activity against virus-infected cells or tumor cells (See Roder J C, Pross H F, J Clin Immunol; 2:249-63, 1982). They have been utilized for treating hematological cancer including acute lymphatic leukemia and myelogenous leukemia (See Fran Romagnet et al., F1000 Medicine Reports; 03:09, 2011). In reality, upon being treated with the persimmon leaf-derived polysaccharide fraction according to an exemplary embodiment, NK cells showed a remarkably increased cytotoxicity against cancer cells (See Example 5).

IL-6 is a cytokine also called "B cell-stimulating factor 2 (BSF2)" or "interferon β2". IL-6 was discovered as a differentiation factor involved in the activation of B lymphocytes (See Hirano, T. et al., Nature 324, 73-76, 1986), followed by a clear finding that it influences the functions of various cells as a multifunctional cytokine (See Akira, S. et al, Adv. in Immunology, 54, 1-78, 1993). IL-6 has been also reported to induce the maturation of T lymphocytes (See Lotz, M. et al., J. Exp. Med. 167, 1253-1258, 1988), while acting on T cells or thymocytes as a co-stimulator to exert an anti-cancer effect (See Kuby J., Immunology, $2^{nd}$ ed, 1994, Chap. 15. W.H. Freemn Company, USA).

It has been reported that IL-12 acts on NK cells and Th 1 cells and thereby induce the production of INF, resulting in differentiating innate forms of NK cells and T cells into their effector forms, which respond to antigens, in the induction of a cell-mediated immunity. Thus, IL-12 is primarily known to activate a cell-mediated immunity involved with Th 1. Therefore, the ability of producing IL-12 from macrophages is considered to be an important factor in activating innate and acquired immunities against antigens (See Dredge K. et al., Cancer Immunol. Immnother. 2002, 51, 521-531, 2002).

It is known that TNF-α possesses a cytotoxicity on certain cancer cells and an antiviral effect, while playing a crucial role in various physiological responses involved with acute and chronic inflammatory diseases (See Kuby J. In 'Immnology' $2^{nd}$ ed. 1994, Chap. 15. W.H. Freeman Company, USA).

The present disclosure provides a method for preparing a persimmon leaf-derived polysaccharide fraction with an immuno-stimulating activity, the method comprising (a) treating a persimmon leaf powder with pectinase; and (b) collecting a fraction having a molecular weight of 3-300 kDa from the enzyme-treated persimmon leaf powder.

Step (a) treating a persimmon leaf with pectinase:

Pectinase is preferably added in an amount of 1-20 wt %, more preferably 5-15 wt %, and most preferably 10 wt %, based on the weight of the persimmon leaf powder. The persimmon leaf as used may be dried or un-dried, and in a pulverized or powdered form. Preferably, the persimmon leaf powder that is treated with the enzyme may be suspended in distilled water at a ratio of 1:5-15 (w/v). Said treatment with the hydrolytic enzyme is preferably performed for 1-5 days, and more preferably 2-4 days. Step (a) further comprises, after treatment with the enzyme, a step of heating the remaining pectinase at a temperature of 90-110° C. for 10-60 minutes to inactivate the enzyme. Due to the heating, the elution of soluble polysaccharide components is increased, and some polymer proteins contained as impurities are modified and precipitated, thereby facilitating the collection of the polysaccharide extract by centrifugation and increasing the purity of the polysaccharide extract.

In addition, step (a) may comprise, before the enzymatic treatment, decolorizing the persimmon leaf powder. A solvent that is used in the decolorizing step may be any decolorizing solvent which is safe and approved for use in the human body. The decolorizing solvent is preferably ethanol, potassium sulfite, sodium sulfite, sulfur dioxide, or benzoyl peroxide, and most preferably ethanol.

Step (b) collecting a fraction having a molecular weight of 3-300 kDa from the enzymatically treated persimmon leaf:

Step (b) is a step of collecting a fraction having a molecular weight of 30-300 kDa from a polysaccharide extract obtained by separating the residue by a method such as centrifugation, solvent fractionation or filtration after the enzymatic treatment. The fraction can be collected by any known purification process which is performed based on a molecular weight. Preferably, the fraction can be collected by ultrafiltration, solvent fractionation or gel filtration chromatography. Most preferably, it can be collected by ultrafiltration. The resulting polysaccharide fraction may be in the form of extract, concentrate, or powder.

The preparation method further comprises step (c) of collecting a fraction having a molecular weight of 5-30 kDa from said collected fraction.

The preparation method may further comprise a step of purification by adding a 50-100% alcohol having 1-4 carbon atoms to the resulting polysaccharide fraction to remove low molecular-weight materials and impurities.

The persimmon leaf-derived polysaccharide fraction according to an exemplary embodiment stimulates the production of IL-6, IL-12 and TNF-α and thereby enhances an immune activity, is not noticeably cytotoxic to macrophages, enhances the activity of Natural Killer cells and inhibits the metastasis of tumor cells. Hence, the persimmon leaf-derived polysaccharide fraction is effective in preparing a food composition for enhancing immunity or improving cancer, and a pharmaceutical composition for preventing or treating a disease caused by a decreased immunity.

Hereinafter, exemplary embodiments will be described in further detail. It is to be understood, however, that the following examples are for illustrative purposes only and are not construed to limit the scope of the present invention.

Example 1: Preparation of Persimmon Leaf-Derived Polysaccharide Fractions

<1-1> Preparation of Non-Enzymatically Treated (Hot Water Extracted) Crude Polysaccharide Fraction (PLW-0)

In this example, persimmon leaves purchased from Baek-Jang-Saeng Co. Ltd. (Yeong-cheon, Gyeongsangbuk-do, Korea) were used in their power form. The powder was added to 90% ethanol at a ratio of 1:10 (w/v), stirred for 48 hours, filtered and dried, followed by decolorization.

The decolorized dry powder was suspended in distilled water at a ratio of 1:10 (w/v) and heated at 100° C. for 3 hours. The hot-water extract was centrifuged at 4° C. and 6,500×g for 15 minutes, and the resulting supernatant as obtained was added to a four-fold volume (v/v) of 80% ethanol and allowed to stand for 24 hours to precipitate polysaccharide. The precipitated polysaccharide was subjected to dialysis (molecular weight cut-off: 6,000-8,000) to obtain a hot-water-extracted crude polysaccharide fraction (PLW-0).

<1-2> Preparation of Enzymatically Treated Crude Polysaccharide Fraction (PLE-0) and Active Polysaccharide Fraction (PLE-II)

The decolorized persimmon leaf dry powder obtained in the same manner as described in Example <1-1> was used.

The decolorized persimmon leaf dry powder was suspended in a 10-fold volume (w/v) of distilled water (pH 4), and pectinase (Rapidase C80MAX, Bision Corp.) was added thereto in an amount of 10 wt % based on the weight of the powder, followed by being treated enzymatically in an incubator at 50° C. for 3 days. Next, the enzymatically treated reaction solution was heated at 101° C. for 30 minutes to extract soluble polysaccharide and inactivate the remaining pectinase.

After the enzymatic treatment, the sample was centrifuged at 4° C. and 6,500×g for 15 minutes to remove residues, and was filtered by ultrafiltration to remove fine materials having a molecular weight of 3 kDa or less, thereby obtaining an enzymatically treated crude polysaccharide fraction (PLE-0).

Ultrafiltration was performed two times on PLE-0 fraction to obtain a polysaccharide fraction having a molecular weight of 3-30 kDa (PLE-II).

Example 2: Analysis of Sugar Composition of Each Fraction

<2-1> Analysis of Sugar Composition

To analyze the sugar composition of each fraction, hydrolysis was performed according to a slight modification to Albersheim et al.'s method, and then each sugar component was derivatized into its corresponding alditol acetate and analyzed by GC (Gas Chromatography). The polysaccharide sample was hydrolyzed in 2M TFA (trifluoroacetic acid) at 121° C. for 1.5 hours, and the hydrolysate was separated into neutral sugar and acidic sugar by Dowex-1 (acetate form) resin. It was dissolved in 1 mL of 1M $NH_4OH$ (ammonia solution) and reduced with 10 mg of $NaBH_4$ for 4 hours. A suitable amount of acetic acid was added thereto to remove the remaining $NaBH_4$. Then, methanol was added thereto, and the solution was repeatedly dried to remove an excess of acetic acid, whereby each sugar component was converted into its corresponding alditol. Then, each alditol was converted into alditol acetate by reacting it with 1 mL of acetic anhydride at 121° C. for 30 minutes. The alditol acetate was separated and extracted with a chloroform/$H_2O_2$ phase solvent system, and the extract was dried, and then dissolved in a small amount of acetone and used as a sample for GC analysis. GC analysis of the alditol acetate derivatives was performed under the conditions described in Table 2 below, and the mole % of each sugar component was determined based on the peak area, molecular weight and molecular response factor for FID (Flame ionization detector) of each derivative.

TABLE 1

| GC analysis conditions | |
| --- | --- |
| Apparatus | GC ACME - 6100 (YoungCo. Ltd., Anyang, Korea) |
| Detector | Flame ionization detector(FID) (Young - Lin Co. Ltd., Anyang, Korea) |
| Column | SP-2380 capillary column (Supelco, Bellefonte, USA) |
| Column size | 0.25 mm × 30 m, 0.2 m film thickness |
| Oven temp. | 60° C.(1 min) 220° C.(12 min) 250° C.(15 min) 30° C./min 8° C./min |
| Injector temp. | 250° C. |
| Detector temp. | 270° C. |
| Carrier gas | N2(1.5 mL/min) |

As a result, polysaccharide fraction (PLE-II) was mainly composed of Rhamnose, Arabinose, Galactose and Galacturonic acid and Glucuronic acid, while comprising rarely observed sugars including 2-methylfucose, 2-methylxylose, apiose, aceric acid, 3-deoxy-D-manno-2-octulosonic acid (KDO) and 3-deoxy-D-lyxo-2-heptulosaricacid (DHA) as Rhamnogalacturonan II (RG-II) indicator materials which are hardly found in nature (See Table 3).

TABLE 2

Sugar composition of the polysaccharide fraction (unit: mole %)

| | PLW-0 | PLE-0 | PLE-II |
| --- | --- | --- | --- |
| Chemical composition (% or weight %) | | | |
| Neutral sugar | 60.4 | 71.3 | 69.5 |
| Uronic acid | 38.3 | 26.2 | 27.2 |
| Protein | 0.0 | 0.7 | 0.0 |
| KDO analogs | 1.3 | 1.8 | 3.3 |
| Components of neutral sugar (mole %) | | | |
| 2-Mefuc | 0.3 | 1.6 | 4.0 |
| Rha | 7.1 | 15.6 | 27.9 |
| Fuc | 1.2 | 2.4 | 4.9 |
| 2-Mexyl | 0.5 | 2.0 | 4.7 |
| Ara | 33.6 | 26.3 | 28.2 |
| Xyl | 5.7 | 6.7 | 0.0 |
| Api | 3.9 | 4.5 | 2.9 |
| Aceric acid | 2.5 | 1.4 | 3.5 |
| Man | 1.2 | 2.1 | 0.4 |
| Gal | 28.5 | 32.3 | 19.6 |
| Glc | 15.5 | 5.1 | 3.9 |

The KDO analogs indicate 3-deoxy-D-manno-2-octulosonic acid (KDO) and 3-deoxy-D-lyxo-2-heptulosaricacid (DHA), while the uronic acid indicates galacturonic acid and glucuronic acid. The content of each component in neutral sugar was expressed based on the total weight of neutral sugar.

<2-2> Analysis of Purity of PLE-II

The purity of the purified PLE-II fraction was analyzed by HPLC. The analysis was performed using Shimadzu LC 6A equipped with Asahipak GS-320+GS220 (each 0.76×50 cm, Asahi Chemical Industry Co., Japan). 0.2M NaCl was used as an elution solvent.

The result is shown in FIG. 1. As shown in FIG. 1, PLE-II showed a symmetric single peak, suggesting that it was purified with a relatively high purity. In addition, the measurement result of the molecular weight using standards (pullulan series) indicated that the molecular weight of PLE-II purified from persimmon leaves was 18 kDa.

Example 3: Toxicity Test of PLE-II Fraction

In order to evaluate the cytotoxicity of test substances on tumor and non-tumor cells, non-tumorous macrophages and tumor cell line Colon 26-M3.1 (RCB2657, Cell Bank, RIKEN Bioresource Center, Tsukuba, Japan) were respectively counted in a concentration of $1×10^4$ cells/mL, followed by being placed into a flat-bottomed 96-well microplate in an amount of 100 ml. Then, 100 nil of persimmon leaf-derived polysaccharide fraction samples (PLE-II), which were prepared in various concentrations, were added to each well and cultured in a 5% $CO_2$ incubator at 37° C. for 3 days. The cytotoxicity of each concentration of test samples was measured by diluting CCK-8 (cell counting kit-8, Dojindo Co, Ltd., Japan) five times and adding test samples in a concentration of 50 ml/well, followed by reacting in a 5% $CO_2$ incubator at 37° C. for 30-60 minutes and measuring the absorbance at 450 nm (See Hwang Y C et al, Korean J Food Sci Technol. 40:220-227, 2008).

The result is shown in FIG. 2 in which the absorbance of control group to which PLE-II fraction was not added was set to 100. As indicated in FIG. 2, it was confirmed that PLE-II fraction was not toxic to macrophages and said tumor cell line.

Example 4: Ability of PLE-II to Stimulate the Production of Cytokines in Macrophages 2 mL of 5% thioglycollate medium was injected intraperitoneally to BALB/c mice (female, 6 weeks old). After 72 hours of their induced production, macrophages were collected from the mice. 100 uL of the macrophages were added to each well of a 96-well well culture plate at a concentration of $2.25×10^5$ cells/mL, and then 100 ul of each sample was added thereto at various concentrations, and the cells were cultured in 5% $CO_2$ incubator at 37° C. for 24 hours. After completion of the culture, the cell culture was centrifuged at 1,500 rpm and 4° C. for 5 minutes. Then, after 150 uL of the cell culture medium solution was collected, the contents of induced cytokines in a supernatant of the cell culture medium solution were measured.

The contents of cytokines produced by macrophages were analyzed by sandwich ELISA (enzyme-immunosorbent assay). An antibody against each cytokine was diluted in coating buffer and coated on a flat 96-well microplate, after which it was allowed to stand at 4° C. for 12 hours. After the completion of coating, the coated microplate was washed three times with washing buffer (PBS with 0.05% tween 20, PBST), and 200 mL of assay diluent (PBS with 10% FBS or 2% skim milk) was added to the plate and allowed to stand for 1 hour to block the surface of wells to which the antibody was not attached. After completion of blocking, each well was further washed three times with washing buffer. 50 mL of each of serially diluted standard material (recombinant mouse cytokine) and the immune cell culture were added to each well, respectively. The plate was allowed to stand at room temperature for 2 hours, and then washed with washing buffer and treated with 100 mL of detection antibody (in assay diluent). Next, the plate was allowed to stand at room temperature for 1 hour, and then washed again. The plate was treated and reacted with 100 mL of enzyme reagent (avidin-horseradish peroxidase conjugate) at room temperature for 30 minutes, and then 100 mL of a substrate solution [tetramethylbenzidine (TMB) and hydrogen peroxide] was added thereto and allowed to react in a dark place for 30 minutes. Next, the plate was treated with 50 mL of stop solution [(1 M $H_3PO_4$ or 2 N $H_2SO_4$)], and the absorbance at 450 nm was measured (See Saike I et al., Vaccine 6: 238-244, 1988).

Figure 3:
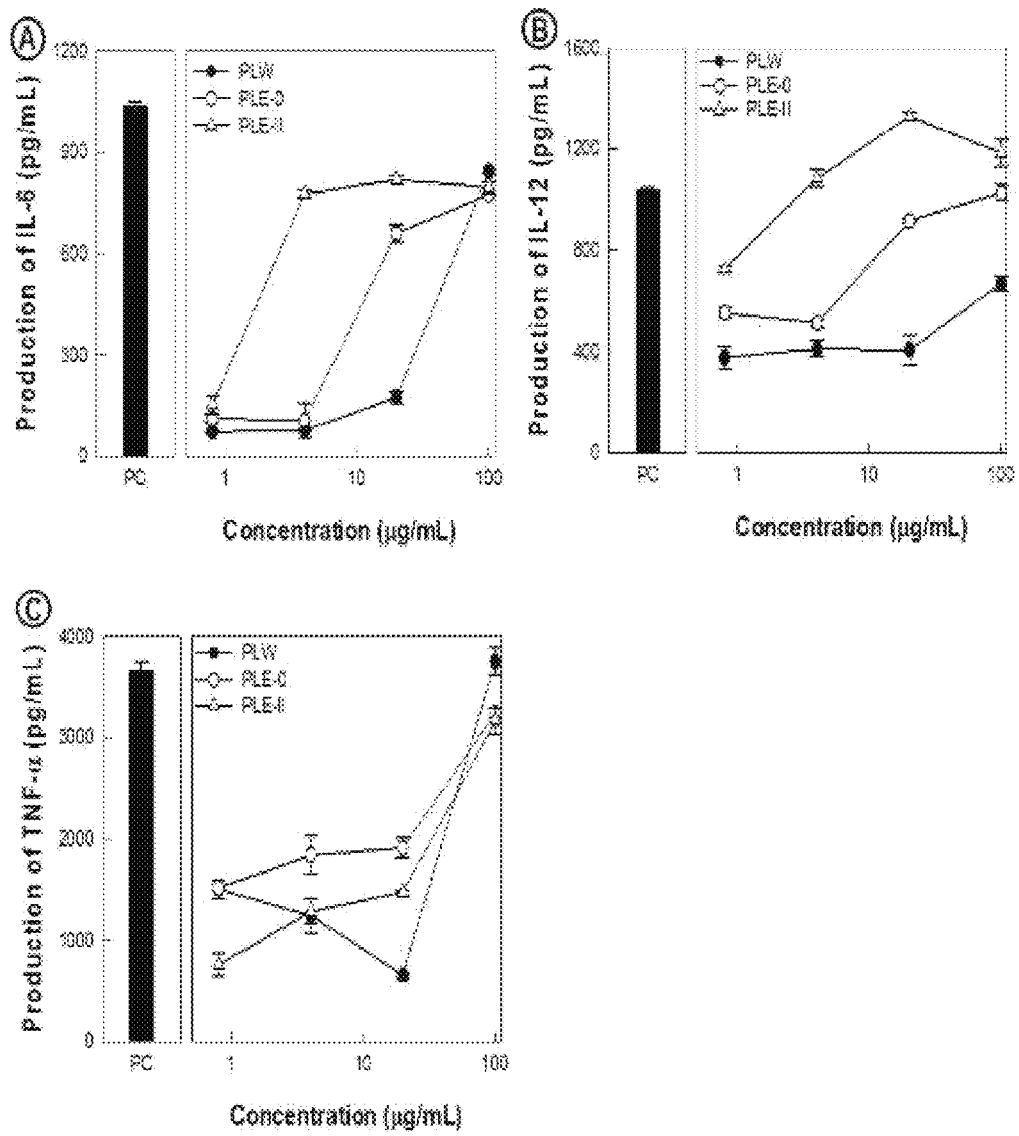
FIG. 3 shows (a) a result of measuring the concentration of cytokine IL-6 produced depending on a concentration of PLE-II fraction, (b) a result of measuring the concentration of cytokine IL-12 produced depending on a concentration of PLE-II fraction, and (c) a result of measuring the concentration of cytokine TNF-α produced depending on a concentration of PLE-II fraction.

FIG. 3 shows the results of measuring the production of cytokines in macrophages caused by the direct stimulation of the persimmon leaf-derived polysaccharide sample. As can be seen in FIG. 3, it was found that PLE-II stimulated the production of IL-6, IL-12 and TNF-α.

As to IL-6, PLE-II showed a high capability of inducing the production of IL-6 in its concentration of 4.0 to 100 μg/ml, which was similar to that of the positive control group of LPS (lipopolysaccharide). While crude polysaccharide fraction obtained from simple water extract (PLW) and one obtained from an enzymatic treatment (PLE-0) also showed the increase of their activity in a concentration dependent way, the amount of IL-6 produced by said crude fractions in their concentration of 100 μg/ml or less was much less than PLE-II. Hence, this result suggested that PLE-II can be very effective in a smaller amount than PLW-0 and PLE-0.

As to IL-12, PLE-II showed an increased production of IL-12 in its concentration of up to 20.0 μg/ml, followed by a slight decrease. However, PLE-II exerted an overall higher expression level of IL-12 than those of PLW and PLE-0. While a similar tendency to IL-12 was detected with regard to TNF-α, PLE-II in its concentration of up to 100 μg/ml showed an increased expression level of TNF-α in a concentration dependent manner.

Example 5: Cancer Cell Cytotoxicity of NK Cells Induced by the Persimmon Leaf-Derived Polysaccharide Fractions <5-1> Effect of PLE-II on Cancer Cell Cytotoxicity of NK Cells 2 mg/kg (weight of mouse) of the persimmon leaf-derived polysaccharide fraction samples was intravenously injected into BALB/c mice (female, 6 weeks old). 3 days later, the mice were sacrificed by cervical dislocation and their spleens were extracted aseptically. Splenocytes were obtained by grinding via stainless steel mash (100 meshes) in PBS (phosphate buffered saline) solution, followed by filtration (200 meshes). 5 ml of 0.2% NaCl was added for 15-30 seconds to destroy mixed red blood cells. Then, splenocytes were washed two or three times with a non-serum culture medium, followed by adjusting their cell count to $1×10^6$ cells/ml and then using as Effector cells.

YAC-1 cells (NK cell-sensitive tumor cell line) were used as Target cells, and were added to round bottomed 96-well microplate in an E/f ratio (a ratio of Effector cell to Target cell) of 100, 50 and 25, respectively. After culturing in a 5% $CO_2$ incubator at 37° C. for 6 hours, the amount of LDH (lactate dehydrogenase) released from the Target cells, which were caused by the cytotoxic activity of the Effector cells, was measured by using Cytotox 96 (Promega Madison, Wis., USA). The cytotoxic activity of NK cells on tumor cells was calculated by a following equation (see Mueller E A et al., J. Immunopharm. 19: 69-77, 1990):

NK cell activity (%)=[(Experimental release amount−Spontaneous release amount)/(Maximal release amount−Spontaneous release amount)]× 100

Spontaneous release amount: the amount of LDH released from Target cells, without the presence of Effector cells Experimental release amount: the amount of LDH released from Target cells, with the presence of Effector cells Maximal release amount: the amount of released LDH after Target cells were cultured with 10% triton X-100

Figure 4:
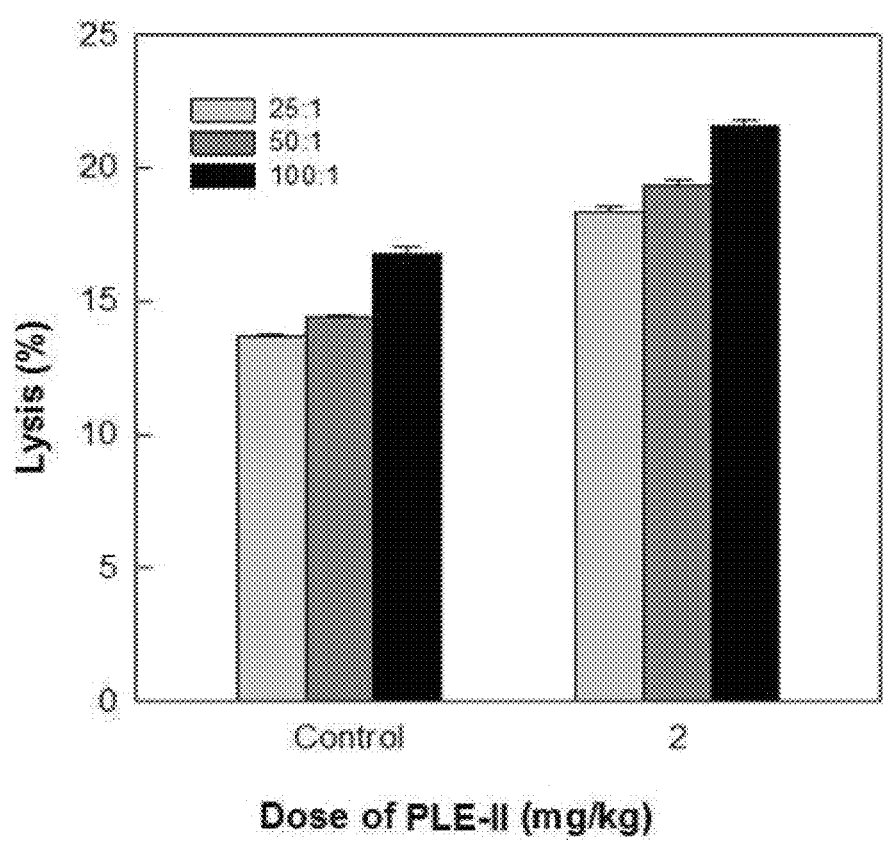
FIG. 4 shows a result of measuring the activity of NK cells depending on a concentration of PLE-II fraction (Lysis (%)—cytotoxicity of NK cell; Dose of sample (mg/Kg)—a treated concentration of PLE-II fraction; Control—a control group without being treated with PLE-II fraction; 100:1, 50:1, 25:1—Elf ratio).

FIG. 4 shows the result regarding the activation of NK cells. It was found that PLE-II was around 26% more effective in inducing the death of the tumor cells than the control group which was not treated with PLE-II.

<5-2> Effect of PLE-0 on Cancer Cell Cytotoxicity of NK Cells 10 and 100 μg/mouse/day of the persimmon leaf-derived polysaccharide fraction samples was orally administered once daily for 20 days to BALB/c mice (female, 6 weeks old). After the completion of oral administration, the mice were sacrificed by cervical dislocation and their spleens were extracted aseptically. Lymphocytes were obtained by grinding via stainless steel mash (100 meshes) in PBS (phosphate buffered saline) solution and filtration (200 meshes). 5 ml of 0.2% NaCl was added for 15-30 seconds and shaken to destroy mixed red blood cells, and then washed three times with a non-serum culture medium, followed by adjusting their cell count to $1\times10^6$ cells/ml with hemacytometer and then using as Effector cells. YAC-1 lymphoma cells (mouse NK cell-sensitive tumor cell line) were used as Target cells, and were added to round bottomed 96-well microplate (Becton Dickinson Labware, Franklin Lakes, N.J., USA) in an E/T ratio (a ratio of Effector cell to Target cell) of 25, 50 and 100, respectively. After culturing in a 5% $CO_2$ incubator at 37° C. for 18-24 hours, they were centrifuged at 1500 rpm for 5 minutes to obtain 100 ml of the supernatant from the culture medium solution. As to the cytotoxic effect of NK cells, the amount of LDH (lactate dehydrogenase) released from the Target cells into the supernatant of the culture medium solution, which was caused by the cytotoxic activity of the Effector cells, i.e. NK cells, was measured by using LDH assay kit (Oxford). The cancer cell cytotoxicity of NK cells was calculated according to said equation as described in Example <5-1>.

Figure 6:
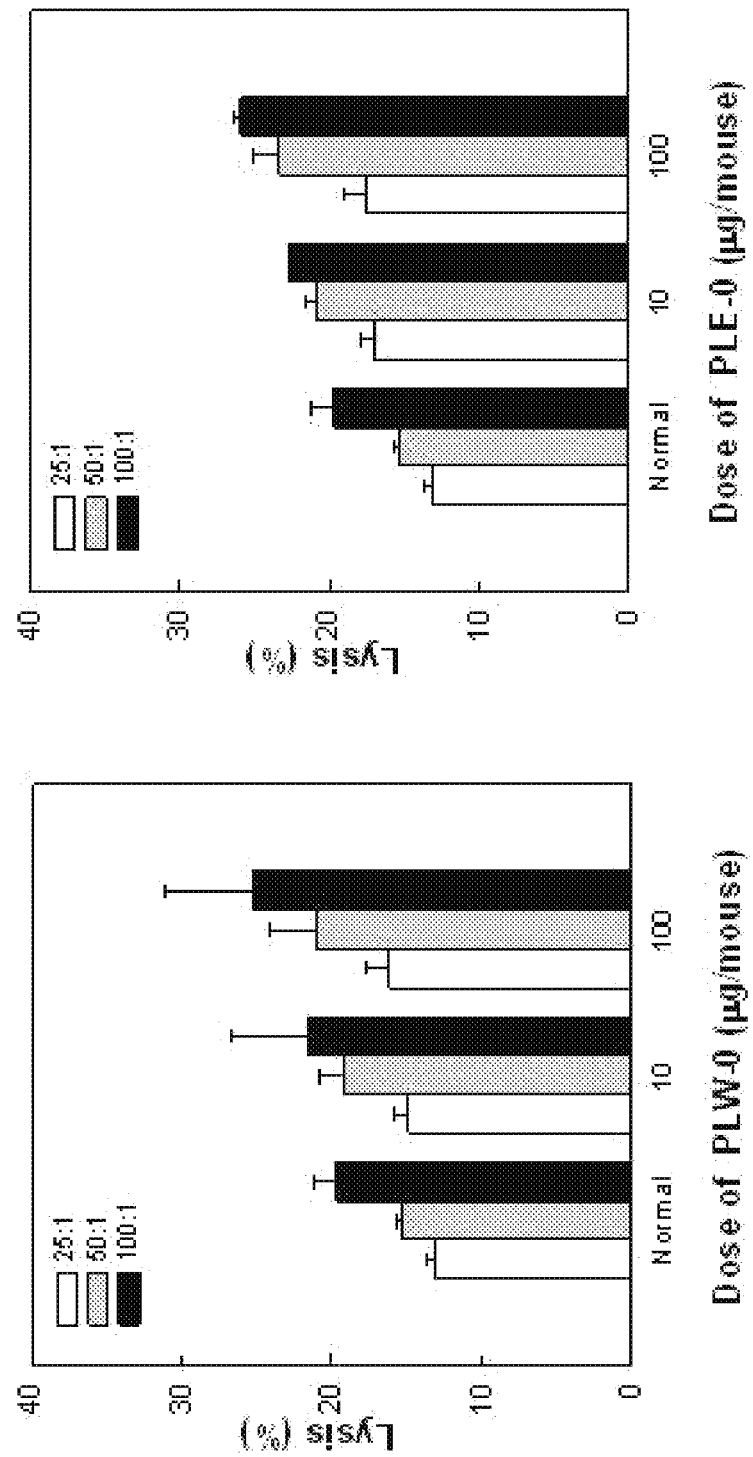
FIG. 6 shows results of the activity of NK cells depending on a concentration of PLW-0 and PLE-0 fractions, respectively (Dose of sample (mg/Kg)—the treated concentration of PLW-0 or PLE-0 fraction; Normal—Control group without being treated with PLW-0 or PLE-0 fraction).

As shown in FIG. 6, the effect of PLE-0 on stimulating the tumor cell cytotoxicity of NK cells was changed in an E/f ratio (Effector cells (splenocytes) to Target cells (YAC-1))-dependent manner. In all of the tested E/f ratios, PLE-0, which was obtained by the enzymatic treatment and the molecular weight fraction, demonstrated higher tumor cell cytotoxicity than PLW-0 obtained by simple hot water extraction. This result confirmed that the persimmon-leaf derived polysaccharide fractions even in their oral administration contribute to activating the tumor cell cytotoxicity of NK cells.

Example 6: Anti-Metastatic Activity of Persimmon Leaf-Derived Polysaccharide

<6-1> Effect of PLE-0 and PLE-II on Anti-Metastatic Activity

Anti-metastatic activity of test substances was examined with a tumor metastasis test animal model by using highly metastatic tumor cell line Colon 26-M3.1. In order to observe the effect of test substances on tumor metastasis, the number of Colon 26-M3.1 carcinoma cells was adjusted to $4\times10^4$ cells/mouse, followed by their intravenous injection into 6 week old female C57BL/6 mice. Test substances were injected in their various concentrations 2 days prior to the administration of said tumor. 14 days after the administration of tumor, mice were sacrificed by cervical dislocation, followed by the extraction of the lungs which were the target of said tumor cells. The tumor cells metastasized to the lungs were fixed and dyed with Bouin's solution (Sigma). The colony of the metastasized tumor was counted. The anti-tumor metastatic activity of test substances was compared with the control group which was administered only with tumor cells (See Ha E S et al., Arch Pharm Res. 27: 217-224 (2004); Yoon T J et al., J. Ethnopharm. 93:247-253 (2004)).

As a result, it was found that an average of 120 colonies were counted in tumor control group. Based on said result, all the test groups of PLW-0 (simple hot water extracted, persimmon leaf-derived crude polysaccharide fraction), PLE-0 (enzymatically treated crude polysaccharide fraction) and PLE-II (enzymatically treated, crude purified polysaccharide fraction) showed 70% or higher of anti-metastatic effect in their concentration of 1,000 μg/mouse (See FIG. 5).

Figure 5:
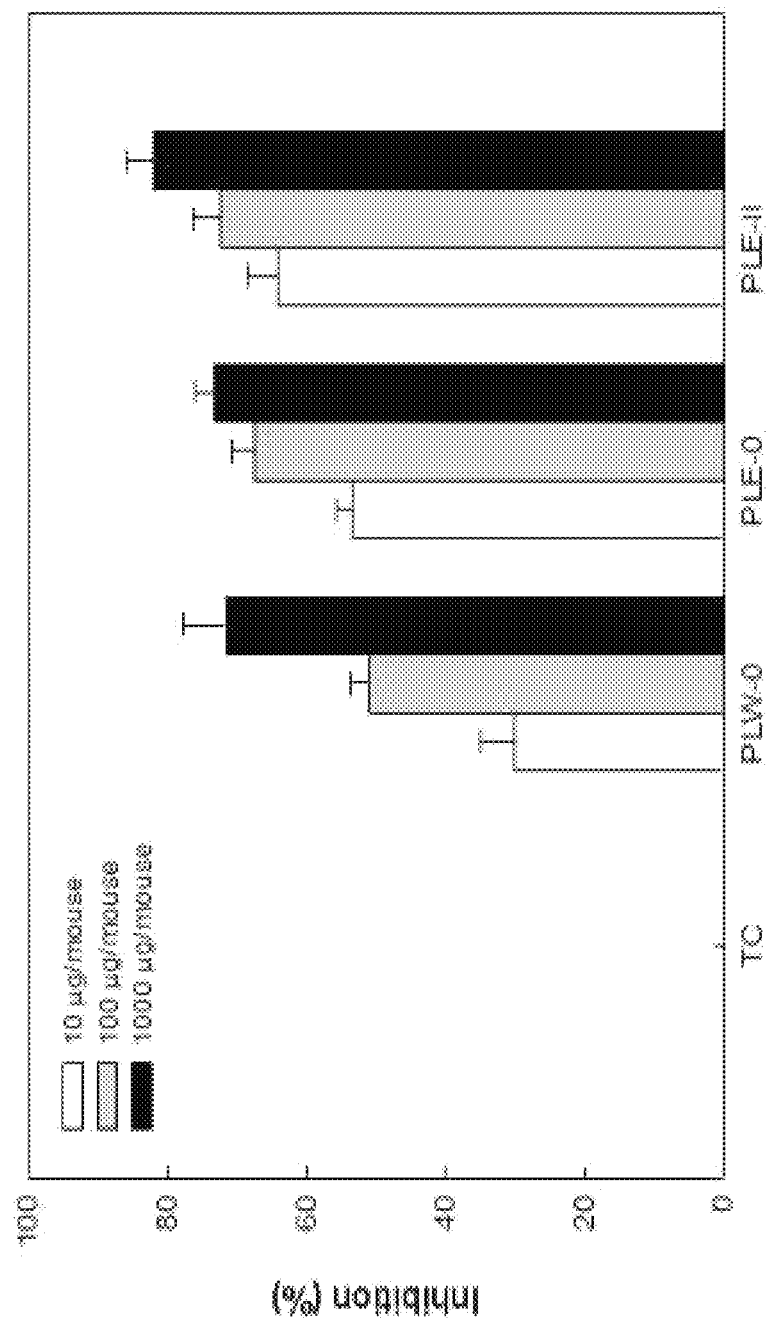
FIG. 5 shows an inhibition rate of cancer metastasis by persimmon leaf-derived polysaccharide fractions (TC: Tumor control group in which only tumor cells were injected.

As shown in FIG. 5, PLE-II exerted the highest activity of 82.2%, while all the test groups showed their anti-metastatic activity in a concentration-dependent manner. Particularly, in a concentration of 10 μg/mouse, PLW-0 exerted 30.2% of anti-metastatic activity, with 53.5% by PLE-0 and 64.2% by PLE-II. This result confirmed that PLE-II possesses greater than two times higher anti-metastatic activity than PLW-0.

<6-2> Effect of the Oral Administration of PLE-0 on Anti-Metastatic Activity 10, 100 and 1000 μg/mouse/day of test substances were intravenously injected 2 days prior to the administration of tumor, or 10 μg/mouse/day of test substances were orally administered once daily for 20 days prior to the administration of tumor, to 6 week old female C57BL/6 mice. After the completion of intravenous or oral administration of test substances, the number of Colon 26-M3.1 carcinoma cells was adjusted to $4\times10^4$ cells/mouse, followed by their intravenous injection, while test substances were orally administered in said concentration up to 9 days on alternating days. 14 days after the injection of tumor cells, mice were sacrificed by cervical dislocation, followed by the extraction of the lungs which were the target of said tumor cells. The tumor cells metastasized to the lungs were fixed and dyed with Bouin's solution (Sigma). The colony of the metastasized tumor was counted. The anti-tumor metastatic activity of test substances was compared with the control group which was administered only with tumor cells. The result is indicated in FIG. 7A and FIG. 7B.

Figure 7A:
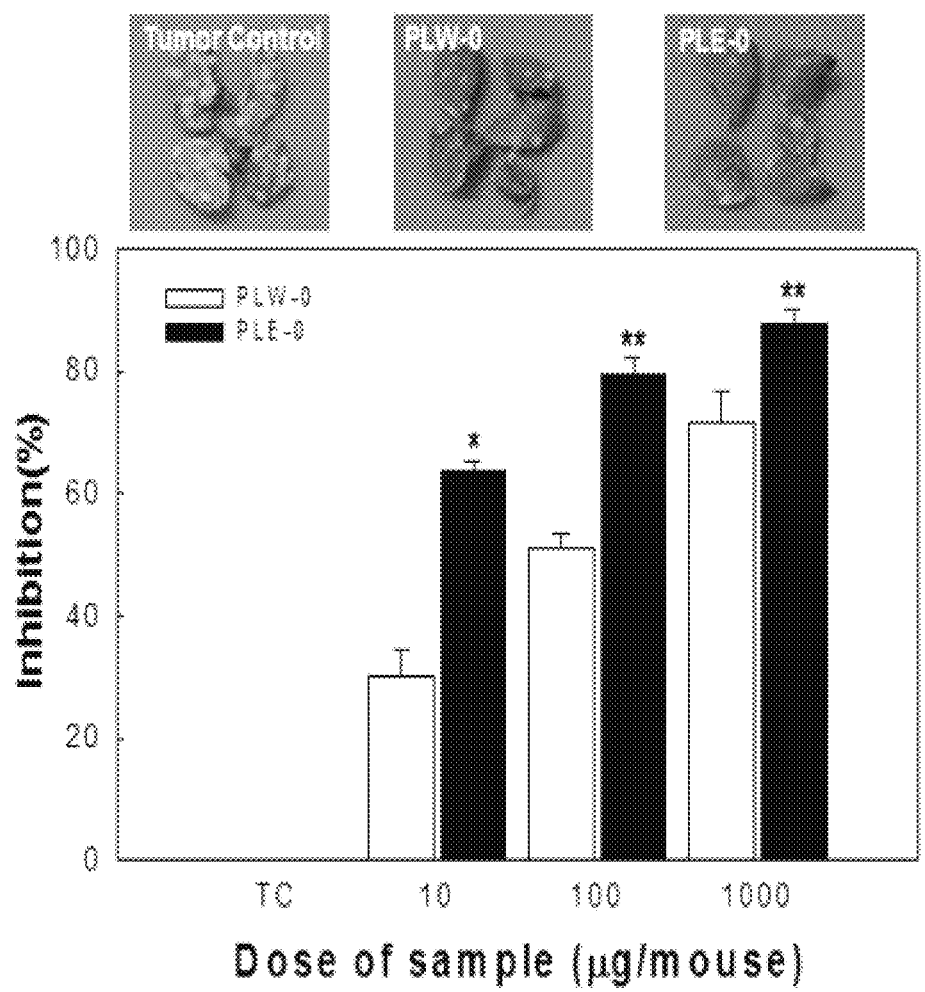
Figure 7B:
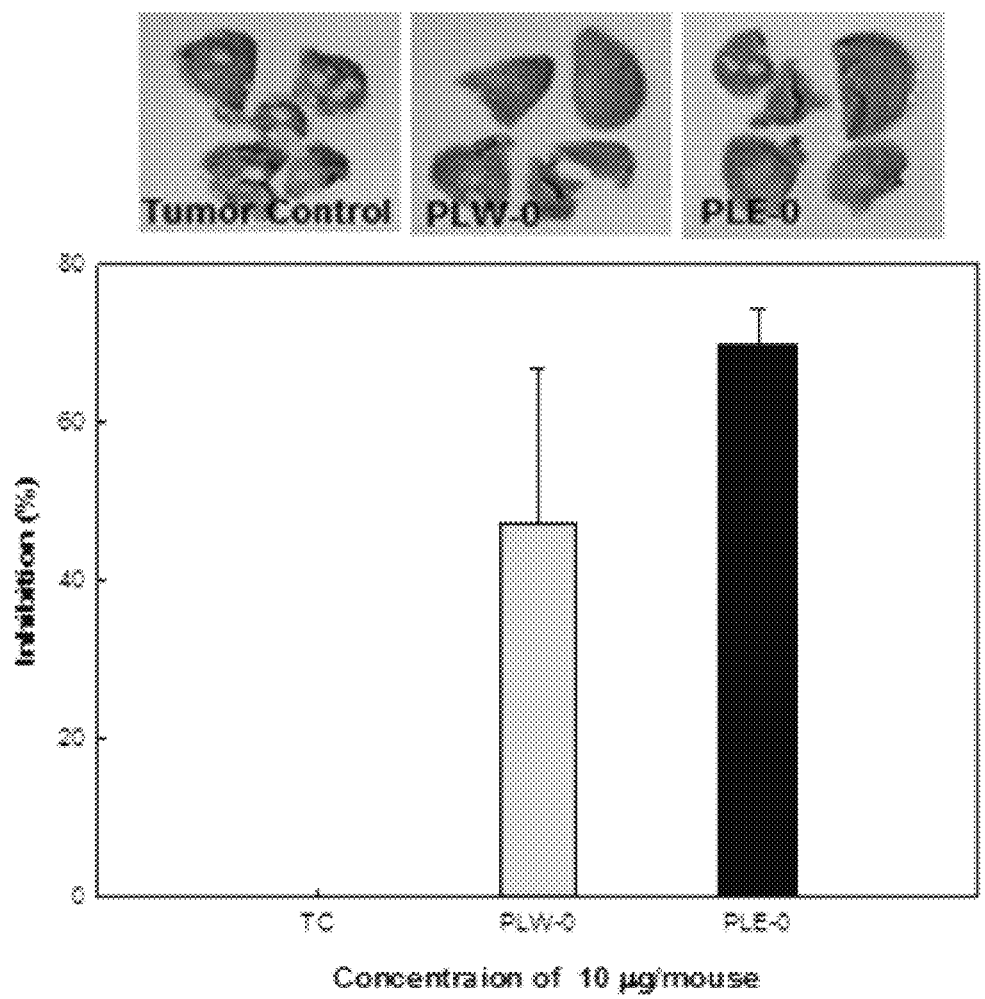
FIG. 7B shows an inhibition rate of cancer metastasis upon their oral administration (Concentration of sample (μg/mouse)–the treated concentration of PLW-0 and PLE-0 fraction).

As a result, FIG. 7A shows that, in comparison with control group without the intravenous administration of test substances, 10 μg of PLW-0 exerted 30.2% of anti-metastatic effect, while the same amount of PLE-0 showed 63.5% of anti-metastatic effect which is almost two times higher than PLW-0. In the case of 1000 μg administration, PLW-0 showed around 71.7% of anti-metastatic activity, with around 87.7% by PLE-0. This result indicates that the enzymatically treated crude polysaccharide fraction is much more potent in its anti-metastatic activity than simple hot water extracted crude polysaccharide fraction. Furthermore, FIG. 7B shows that, upon their oral administration of persimmon leaf-derived polysaccharide fractions, the anti-metastatic activity of PLW-0 was 47.1%, while that of PLE-0 was high being around 70%.

The persimmon leaf-derived polysaccharide fraction according to an exemplary embodiment stimulates the production of IL-6, IL-12 and TNF-α and thereby enhances an immune activity, is not noticeably cytotoxic to macrophages, enhances the activity of Natural Killer cells and inhibits the metastasis of tumor cells. Hence, the persimmon leaf-derived polysaccharide fraction is effective in preparing a food composition for enhancing immunity or improving cancer, and a pharmaceutical composition for preventing or treating a disease caused by a decreased immunity.

What is claimed is:

1. A persimmon leaf-derived polysaccharide fraction consisting of 60-80 wt % of neutral sugar and 18-39 wt % of uronic acid, and 0.5-10 wt % of 3-deoxy-D-manno-2-octulosonic acid (KDO) analogs,
   wherein the wt % is based on the total weight of the polysaccharide fraction,
   wherein the persimmon leaf-derived polysaccharide fraction is prepared by a method comprising:
   (a) treating a persimmon leaf powder with pectinase;
   (b) collecting a fraction having a molecular weight in a range of 3 to 300 kDa from an enzymatically treated persimmon leaf powder; and
   (c) collecting a fraction having a molecular weight in a range of 5 to 30 kDa from the collected fraction in step (b),
   wherein the neutral sugar comprises 20-40 mole % of arabinose, 10-40 mole % of rhamnose, 10-40 mole % of galactose, 1-10 mole % of fucose, 1-10 mole % of glucose, and 0.4-26 mole % of Rhamnogalacturonan-II indicator polysaccharides,
   wherein mole % is based on the total mole of the neutral sugar in the persimmon leaf-derived polysaccharide fraction, and
   wherein the persimmon leaf-derived polysaccharide fraction has a molecular weight of 5-30 kDa.

2. The persimmon leaf-derived polysaccharide fraction of claim 1, wherein the uronic acid consists of galacturonic acid and glucuronic acid.

3. The persimmon leaf-derived polysaccharide fraction of claim 1, wherein KDO analogs consist of 3-deoxy-D-lyxo-2-heptulosaric acid (DHA) and KDO.

4. The persimmon leaf-derived polysaccharide fraction of claim 1, wherein:
   the Rhamnogalacturonan-II indicator polysaccharides consist of 0.1-8 mole % of 2-methylfucose, 0.1-8 mole % of 2-methylxylose, 0.1-5 mole % of apiose, and 0.1-5 mole % of aceric acid; and
   mole % is based on the total mole of the neutral sugar in the persimmon leaf-derived polysaccharide fraction.

5. The persimmon leaf-derived polysaccharide fraction of claim 1, wherein the persimmon leaf-derived polysaccharide fraction possesses an activity of enhancing immunity.

6. The persimmon leaf-derived polysaccharide fraction of claim 1, wherein the persimmon leaf-derived polysaccharide fraction possesses an activity of inhibiting a metastasis of cancer.

7. A food composition for enhancing immunity comprising the persimmon leaf-derived polysaccharide fraction of claim 1 as an active ingredient.

8. A food composition for preventing or improving cancer comprising the persimmon leaf-derived polysaccharide fraction of claim 1 as an active ingredient.

9. An anti-cancer adjuvant preparation comprising the persimmon leaf-derived polysaccharide fraction of claim 1 as an active ingredient.

* * * * *